United States Patent
Hoshino

(10) Patent No.: US 9,241,612 B2
(45) Date of Patent: Jan. 26, 2016

(54) BENDING OPERATION APPARATUS FOR ENDOSCOPE AND ENDOSCOPE INCLUDING THE BENDING OPERATION APPARATUS

(71) Applicant: OLYMPUS MEDICAL SYSTEMS CORP., Tokyo (JP)

(72) Inventor: Yuki Hoshino, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 142 days.

(21) Appl. No.: 14/257,276

(22) Filed: Apr. 21, 2014

(65) Prior Publication Data

US 2014/0296640 A1    Oct. 2, 2014

Related U.S. Application Data

(63) Continuation of application No. PCT/JP2013/076867, filed on Oct. 2, 2013.

(51) Int. Cl.
*A61B 1/005* (2006.01)
*A61B 1/05* (2006.01)

(52) U.S. Cl.
CPC ............. *A61B 1/0052* (2013.01); *A61B 1/05* (2013.01)

(58) Field of Classification Search
CPC .. A61B 1/0052; A61B 1/0016; A61B 1/0057; A61B 1/0055
USPC .................................. 600/146, 147
See application file for complete search history.

(56) References Cited

FOREIGN PATENT DOCUMENTS

| JP | 07-261098 A | 10/1995 |
|----|-------------|---------|
| JP | 10-286220 A | 10/1998 |
| JP | 2002-034902 A | 2/2002 |
| JP | 2003-061903 A | 3/2003 |
| JP | 2004313807 | * 11/2004 |
| JP | 2011-030866 A | 2/2011 |

* cited by examiner

*Primary Examiner* — Anhtuan T Nguyen
*Assistant Examiner* — Rajaa El Alami
(74) *Attorney, Agent, or Firm* — Scully, Scott, Murphy & Presser, P.C.

(57) ABSTRACT

A bending operation apparatus for an endoscope includes a bending operation knob, a first movable disk, a second movable disk, a cam member, a fixed disk, an annular member, and a step portion that is provided at the annular member and comes into contact with a base portion of the cam member as the cam member is pivoted in another direction to cause the second movable disk to move from a second position to a first position.

8 Claims, 11 Drawing Sheets

BENDING OPERATION APPARATUS FOR ENDOSCOPE AND ENDOSCOPE INCLUDING THE BENDING OPERATION APPARATUS

CROSS REFERENCE TO RELATED APPLICATION

This application is a continuation application of PCT/JP2013/076867 filed on Oct. 2, 2013 and claims benefit of Japanese Application No. 2012-234942 filed in Japan on Oct. 24, 2012, the entire contents of which are incorporated herein by this reference.

BACKGROUND OF THE INVENTION

1. Field of the Invention

The present invention relates to a bending operation apparatus for an endoscope that is provided in an operation portion of the endoscope and causes a bending portion of an insertion portion of the endoscope to bend, and to the endoscope including the bending operation apparatus.

2. Description of the Related Art

In recent years, endoscopes have been widely used in the medical field and the industrial field. The endoscope for use in the medical field is capable of observing organs in a body cavity with an elongated insertion portion inserted into the body cavity that is a subject. The endoscope for use in the medical field is also capable of performing various treatments by using as necessary a treatment instrument inserted into an insertion channel included in the endoscope.

With the endoscope for use in the industrial field, the elongated insertion portion of the endoscope can be inserted into an object such as a jet engine and pipes in a factory, thereby allowing to perform inspections such as observations of scratches and corrosions of a region to be inspected in the object, and various treatments with respect to the region to be inspected in the object.

A configuration is well-known in which a bending portion bendable in plural directions is provided to the insertion portion of the endoscope. The bending portion improves the advanceability of the insertion portion in a crooked portion in a duct and renders variable the observation direction of an observation optical system provided at a distal end portion located on a distal end side in an inserting direction with respect to the bending portion (hereinafter referred to as "distal end side"), in the insertion portion.

The bending portion provided at the insertion portion of the endoscope is typically configured to be bendable in four directions, for example, up, down, right and left directions, with a plurality of bending pieces being connected along the inserting direction of the insertion portion. The bending portion is bendable in any of the up, down, right and left directions by a bending operation apparatus provided in an operation portion pulling any of four wires which are inserted through in the insertion portion and which have distal ends in the inserting direction (hereinafter referred to as "distal ends") fixed to a bending piece located on the distal-most end side of the bending pieces.

Specifically, the bending portion has a configuration in which an up-and-down bending sprocket provided in the operation portion is pivoted through a pivoting operation by a bending operation knob for up-and-down bending provided in the operation portion, to pull an upside chain part or a downside chain part of an up and down bending chain wound around the sprocket, thereby pulling an upper or lower wire so that the bending portion is bent in either an up or down direction.

Further, the bending portion has a configuration in which a right-and-left bending sprocket provided in the operation portion is pivoted through a pivoting operation by a bending operation knob for right-and-left bending provided in the operation portion, to pull a right chain part or a left chain part of a right-and-left bending chain wound around the sprocket, thereby pulling a right or left wire, so that the bending portion is bent in either a right or left direction.

A configuration is also well-known in which the operation portion is provided with an up-and-down bending lock lever that fixes a bending angle of the bending portion that is bent in an up or down direction by the pivoting operation of the bending operation knob for up-and-down bending, namely, fixes the pivoting position of the bending operation knob for up-and-down bending. A configuration is also well-known in which the operation portion is provided with a right-and-left lock knob that fixes the bending angle of the bending portion that is bent in a right or left direction by the pivoting operation of a bending operation knob for right-and-left bending, namely, fixes the pivoting position of the bending operation knob for right-and-left bending. The configurations of the lock knob are disclosed in Japanese Patent Application Laid-Open Publication No. 10-286220, for example.

Japanese Patent Application Laid-Open Publication No. 10-286220 discloses a configuration in which the space inside the bending operation knob for up-and-down bending is provided with a friction member that comes into contact with an inner circumferential surface of the knob, and a movable member and a fixed member which are capable of sandwiching the friction member and fixed to the up-and-down lock lever.

When the pivoting position of the bending operation knob for up-and-down bending is fixed using the configuration disclosed in Japanese Patent Application Laid-Open Publication No. 10-286220, the up-and-down lock lever is rotated in one direction along with the lock lever to move the movable member with respect to the fixed member by employing a screw mechanism, to cause the friction member to be sandwiched between the fixed member and the movable member to be elastically deformed, so that the friction member is caused to come into contact with the inner circumferential surface of the bending operation knob for up-and-down bending by a frictional force. Thus, the pivoting position of the bending operation knob for up-and-down bending is fixed by the frictional force.

Note that in Japanese Patent Application Laid-Open Publication No. 10-286220, the configuration in which the pivoting position of the bending operation knob for right-and-left bending is fixed is similar to the configuration in which the pivoting position of the bending operation knob for up-and-down bending is fixed.

Such a configuration for a small bending operation apparatus may also be possible in which the pivoting position of the bending operation knob can be properly fixed with a weak force without a positional variation every time the bending operation knob is used, by using cam grooves instead of the screw mechanism to move two movable disks so as to have a small gap between the movable disks, so that the movable disks sandwich a fixed disk that applies a frictional force to the pivoting of the bending operation knob.

SUMMARY OF THE INVENTION

A bending operation apparatus for an endoscope according to one aspect of the present invention includes: a bending operation knob that is pivotable about a pivoting shaft and performs a bending operation of a bending portion of the endoscope; a first movable disk that is provided inside the bending operation knob; a second movable disk that is movable between a first position in which the second movable disk is separated from the first movable disk by a first gap in an axial direction and a second position in which the second movable disk is separated from the first movable disk by a second gap that is shorter than the first gap in the axial direction; a cam member that is disposed in a position where the cam member contacts the second movable disk, the cam member causing an inclined surface formed on a cam groove to come into contact with the second movable disk as the cam member is pivoted in one direction, to move the second movable disk from the first position to the second position; a fixed disk that is disposed to be in contact with an inner circumferential surface of the bending operation knob, the fixed disk being sandwiched by the first movable disk and the second movable disk in the second position to apply a frictional force to pivoting of the bending operation knob; an annular member that is provided integrally with the second movable disk and is movable along with the second movable disk in the axial direction; and a step portion that is provided at the annular member, the step portion coming into contact with a base portion of the cam member as the cam member is pivoted in another direction, to cause the second movable disk to move from the second position to the first position.

Further, an endoscope including the bending operation apparatus according to one aspect of the present invention includes the bending operation apparatus for the endoscope according to the one aspect.

DETAILED DESCRIPTION OF THE PREFERRED EMBODIMENT

Hereinafter, an embodiment of the present invention will be described with reference to the drawings. It should be noted that the drawings are schematic and relations between thicknesses and widths of respective members, ratios of the thicknesses of the respective members, and the like are different from real ones. It goes without saying that different drawings contain portions of elements having different relations and ratios of dimensions.

Figure 1:
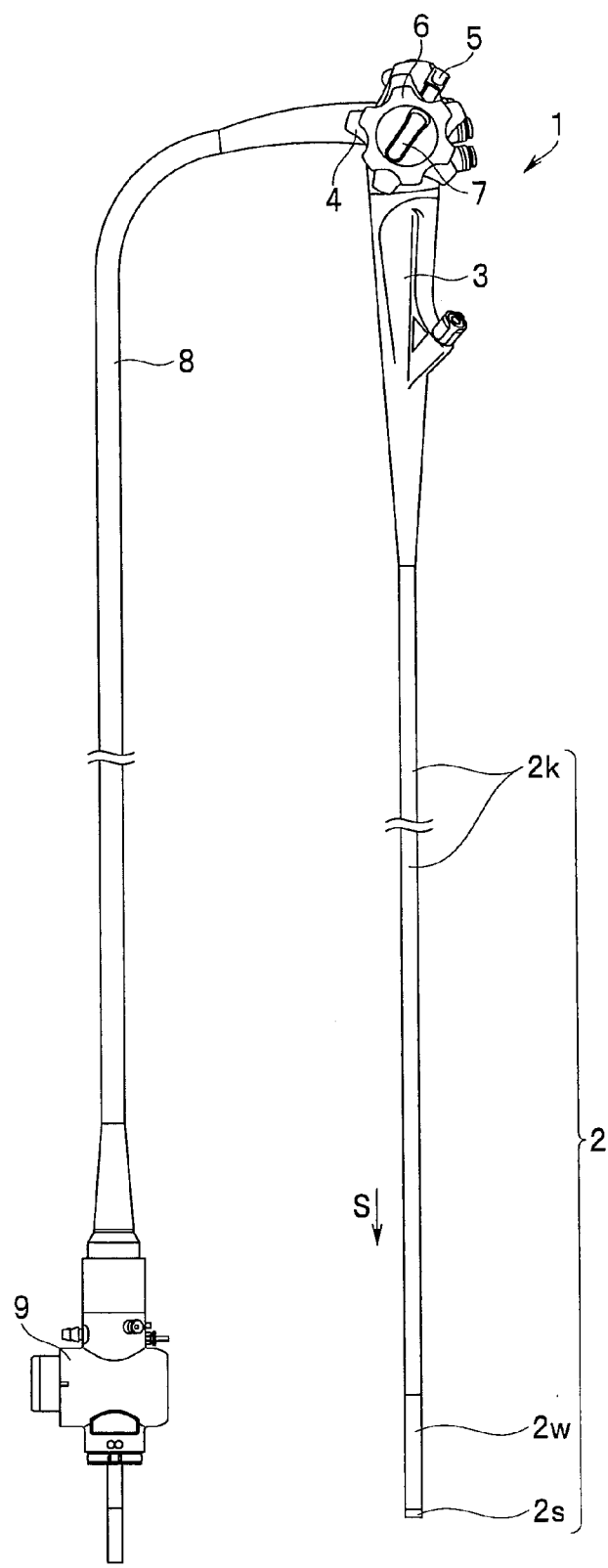
FIG. 1 is a view showing an external appearance of an endoscope having an operation portion including a bending operation apparatus according to the present embodiment.

FIG. 1 is a view showing an external appearance of an endoscope having an operation portion including a bending operation apparatus according to the present embodiment.

As shown in FIG. 1, the main part of the endoscope 1 includes an insertion portion 2 to be inserted into a subject, an operation portion 3 connected on a proximal end side in an inserting direction S of the insertion portion 2, a universal cord 8 extended from the operation portion 3, and a connector 9 provided at an extended end of the universal cord 8. The endoscope 1 is electrically connected with external apparatuses such as a control apparatus and a lighting apparatus via the connector 9.

The operation portion 3 is provided with an up-and-down bending operation knob (hereinafter referred to as "bending operation knob") 4 that causes a bending portion 2w to be described later, of the insertion portion 2 to bend in an up-and-down direction, and a right-and-left bending operation knob (hereinafter referred to as "bending operation knob") 6 that causes the bending portion 2w to bend in a right-and-left direction.

Furthermore, the operation portion 3 is provided with a fixing lever 5 that fixes a pivoting position of the bending operation knob 4 and a fixing knob 7 that fixes a pivoting position of the bending operation knob 6.

Note that the bending operation knob 4, the fixing lever 5, the bending operation knob 6, and the fixing knob 7 constitute a bending operation apparatus 100 (see FIG. 2) to be described later according to the present embodiment, together with other members provided in the operation portion 3.

The insertion portion 2 is constituted of a distal end portion 2s, the bending portion 2w, and a flexible tube portion 2k, and formed to be elongate along the inserting direction S.

In the distal end portion 2s are provided an image pickup unit (not shown) for observing the inside of a subject, an illumination unit that illuminates the inside of the subject, and the like.

Further, the bending portion 2w renders variable the observation direction of the image pickup unit provided at the distal end portion 2s and improves insertability of the distal end portion 2s into the subject, by being bent in four directions, for example, up, down, right and left directions, through pivoting operations of the bending operation knob 4 and the bending operation knob 6. Furthermore, on a proximal end side of the bending portion 2w, the flexible tube portion 2k is connectively provided.

Next, a configuration of the bending operation apparatus 100 for the endoscope provided in the operation portion 3 will be described with reference to FIGS. 2 to 15.

Figure 2:
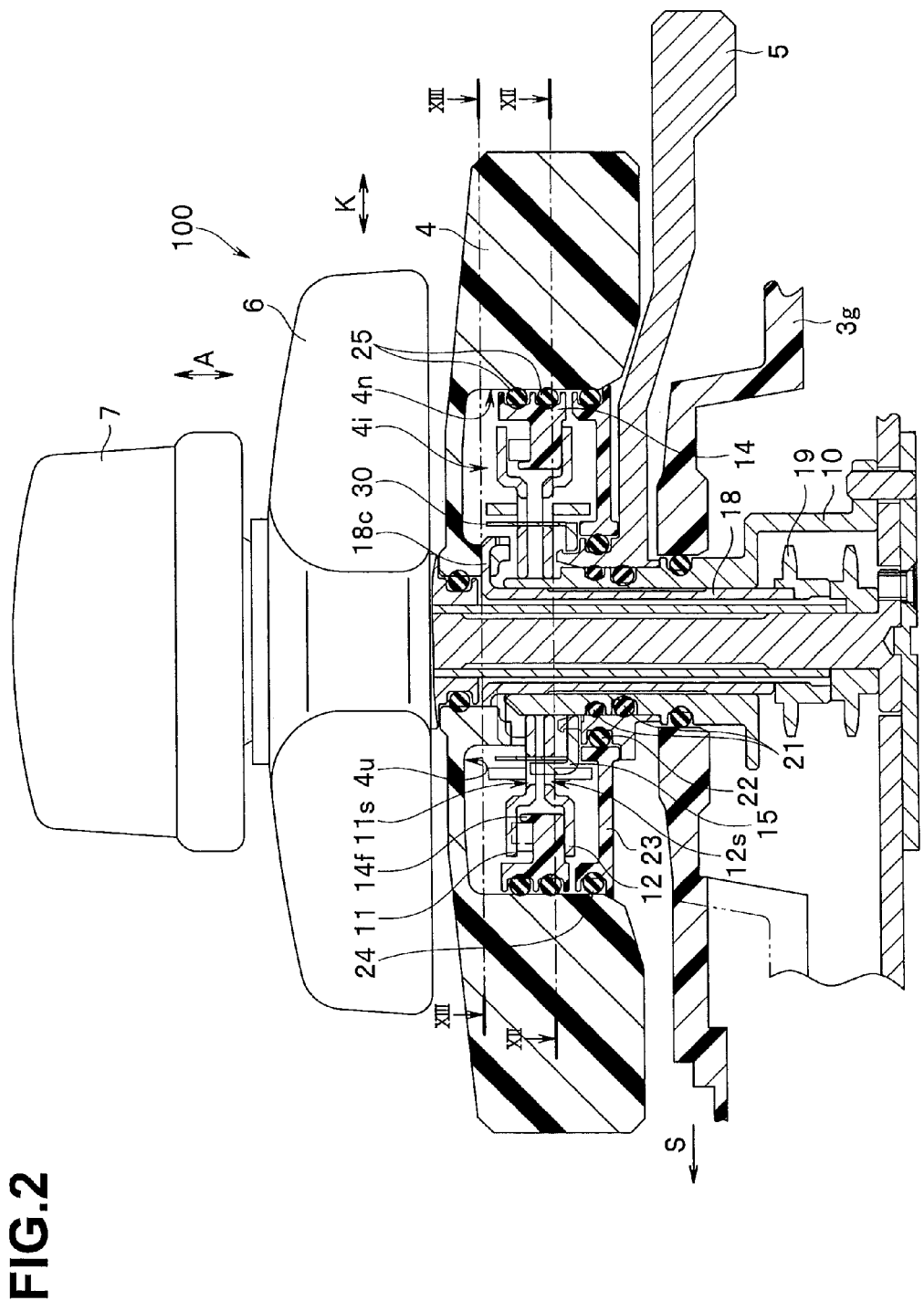
FIG. 2 is a partial sectional view showing a configuration of the bending operation apparatus provided in the operation portion of the endoscope in FIG. 1.
Figure 3:
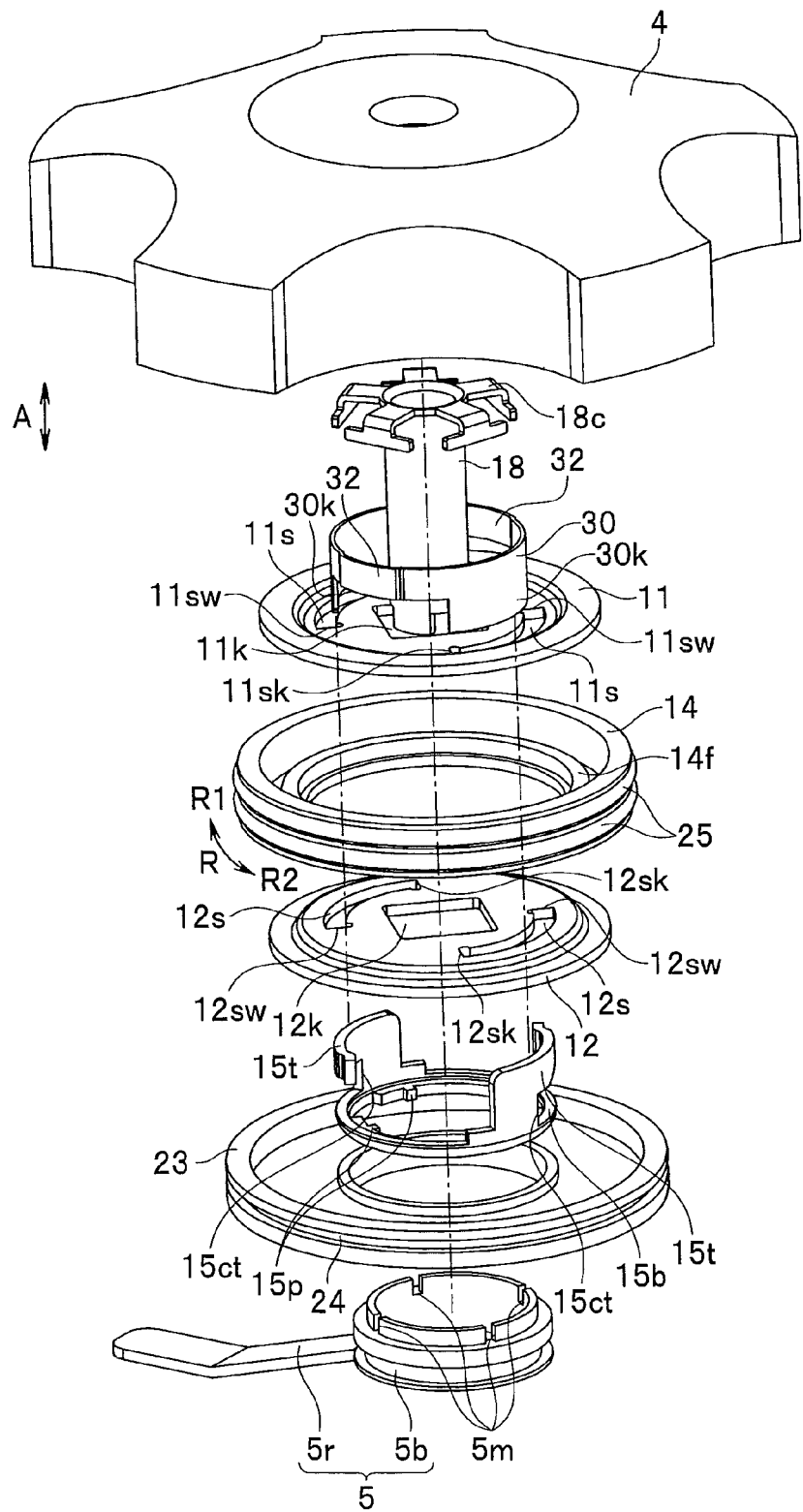
FIG. 3 is an exploded perspective view showing a part of the configuration of the bending operation apparatus in FIG. 2.

FIG. 2 is a partial sectional view showing the configuration of the bending operation apparatus provided in the operation portion of the endoscope in FIG. 1. FIG. 3 is an exploded perspective view showing a part of the configuration of the bending operation apparatus in FIG. 2.

Figure 4:
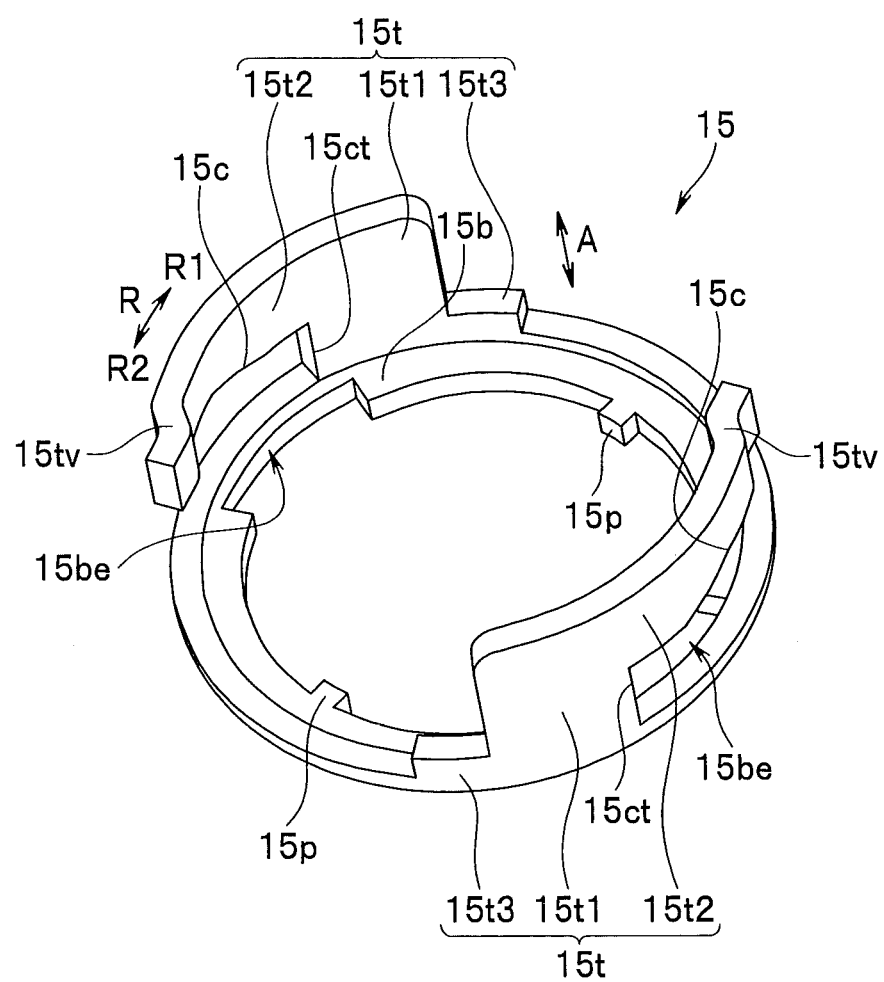
FIG. 4 is an enlarged perspective view showing the cam member in FIG. 3.
Figure 5:
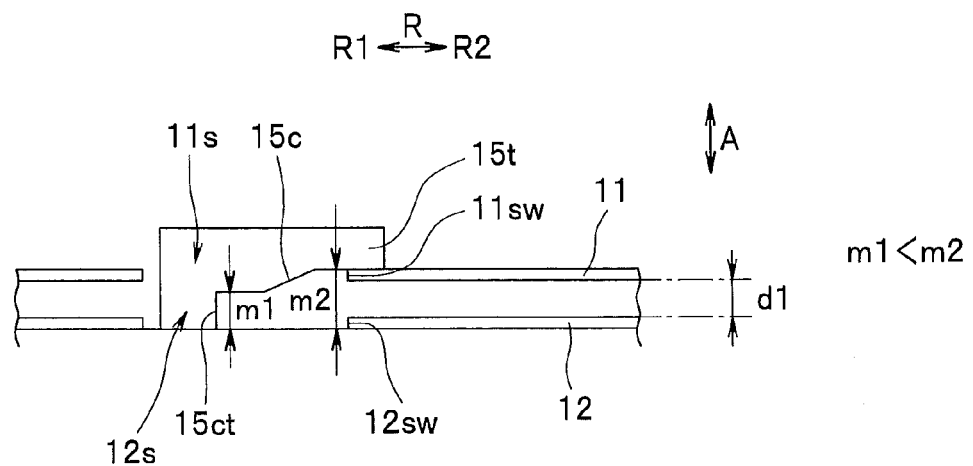
FIG. 5 is a view schematically showing a state in which parts of two movable disks are assembled so as to be fitted in cam grooves provided in protruding portions of the cam member in FIG. 4, having a first gap between the two movable disks.
Figure 6:
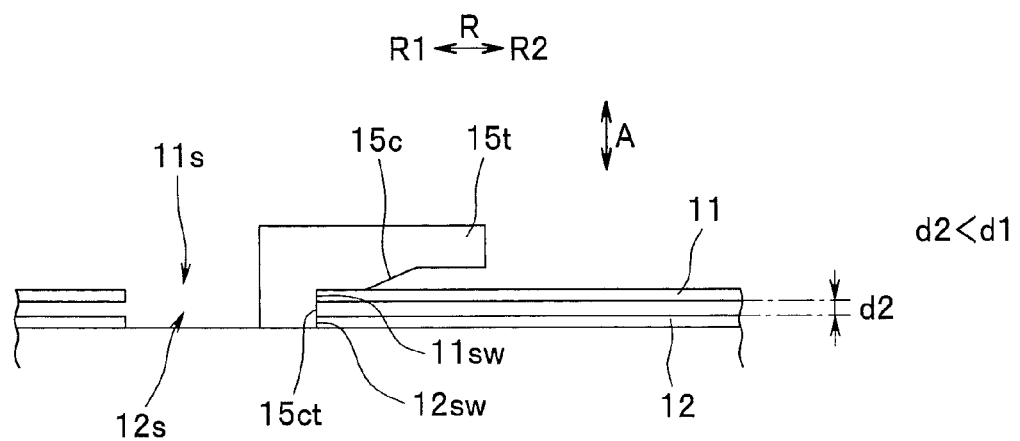
FIG. 6 is a view schematically showing a state in which the two movable disks in FIG. 5 are moved to a position where the disks have a second gap by the cam grooves as the cam member is rotated.

FIG. 4 is an enlarged perspective view showing the cam member in FIG. 3. FIG. 5 is a view schematically showing a state in which parts of two movable disks are assembled so as to be fitted in cam grooves provided in protruding portions of the cam member in FIG. 4, having a first gap between the two movable disks. FIG. 6 is a view schematically showing a state in which the two movable disks in FIG. 5 are moved to a position where the disks have a second gap by the cam grooves as the cam member is rotated.

Figure 7:
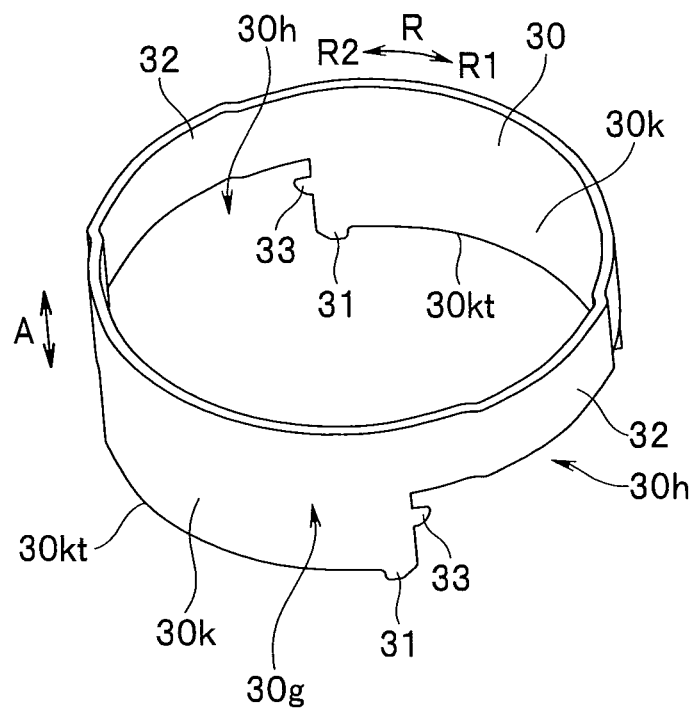
FIG. 7 is an enlarged perspective view showing the annular member in FIG. 3.
Figure 8:
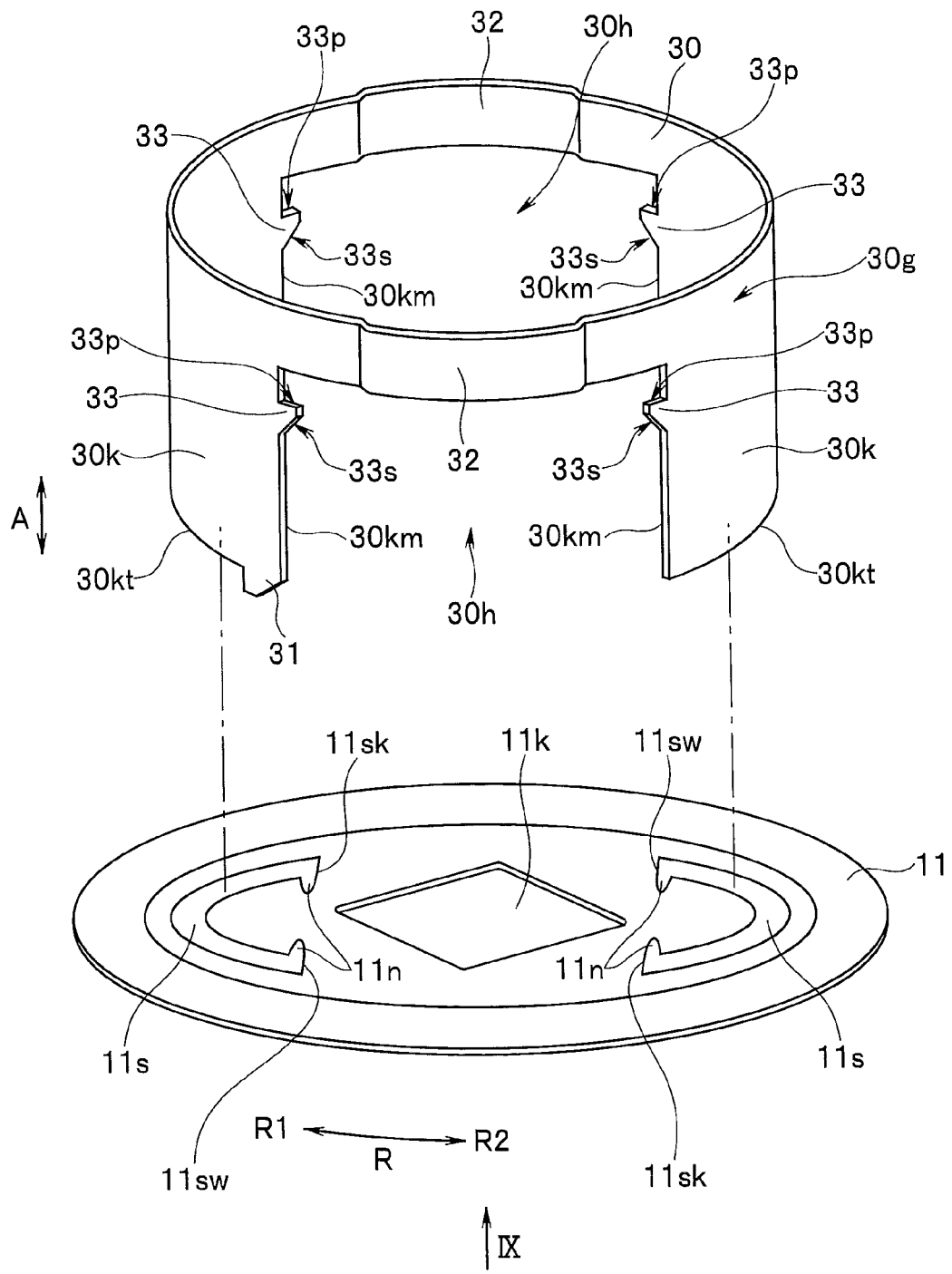
FIG. 8 is an exploded perspective view showing the annular member in FIG. 7 and an upper movable disk.
Figure 9:
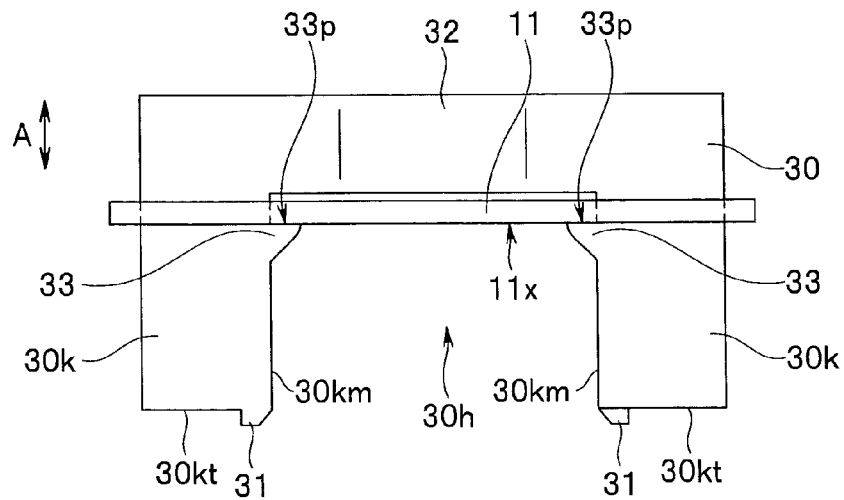
FIG. 9 is a view showing a state in which the upper movable disk is fitted to the annular member in FIG. 8 as viewed from the IX direction in FIG. 8.

FIG. 7 is an enlarged perspective view showing the annular member in FIG. 3. FIG. 8 is an exploded perspective view showing the annular member in FIG. 7 and an upper movable disk. FIG. 9 is a view showing a state in which the upper movable disk is fitted to the annular member in FIG. 8 as viewed from the IX direction in FIG. 8.

Figure 10:
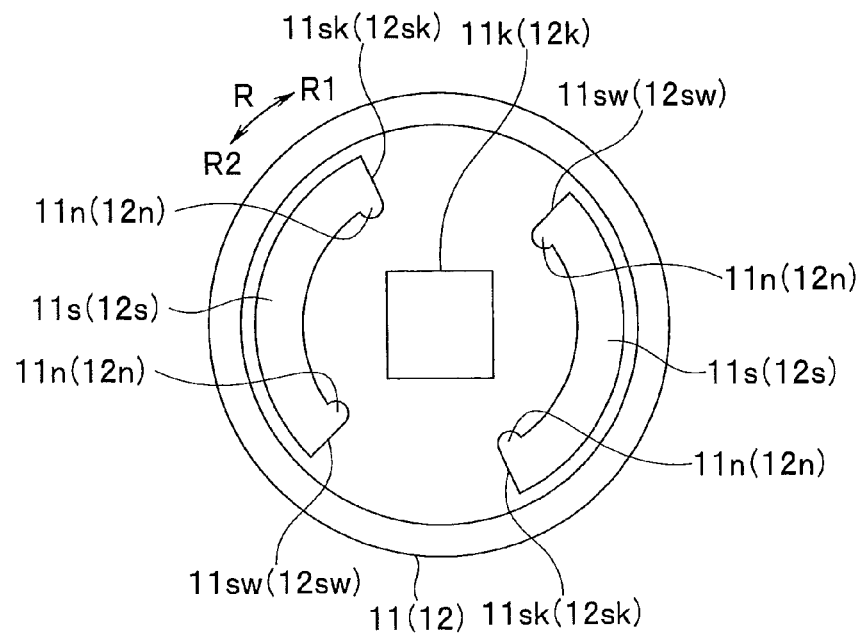
FIG. 10 is an enlarged plan view showing the upper movable disk or the lower movable disk in FIG. 3.
Figure 11:
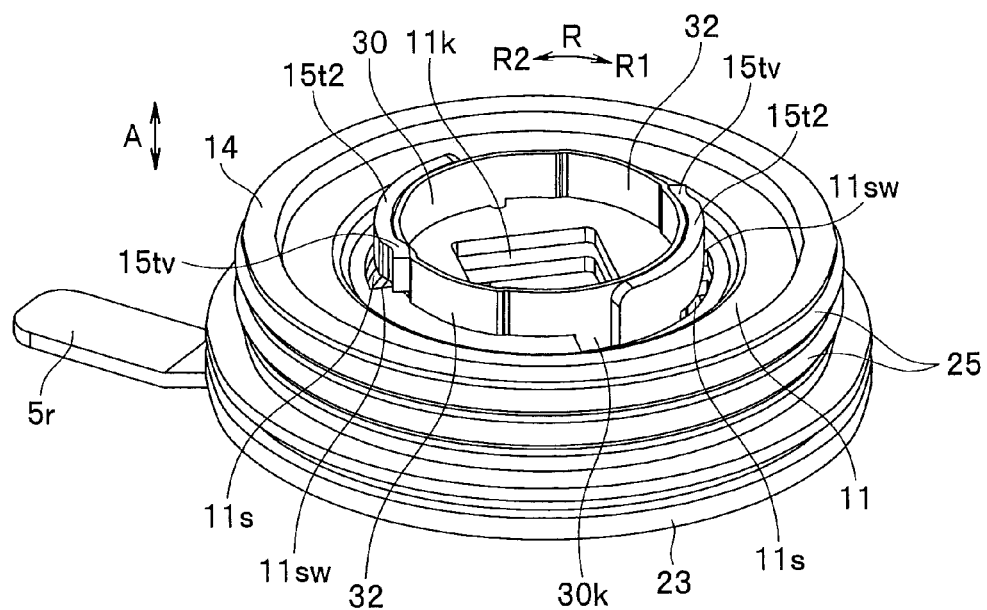
FIG. 11 is an enlarged perspective view showing a state in which the cam member, the annular member, the two movable disks, the fixed disk, the support plate, and the fixing lever in FIG. 3 are assembled together.

FIG. 10 is an enlarged plan view showing the upper movable disk or the lower movable disk in FIG. 3. FIG. 11 is an enlarged perspective view showing a state in which the cam member, the annular member, the two movable disks, the fixed disk, the support plate, and the fixing lever in FIG. 3 are assembled together.

Figure 12:
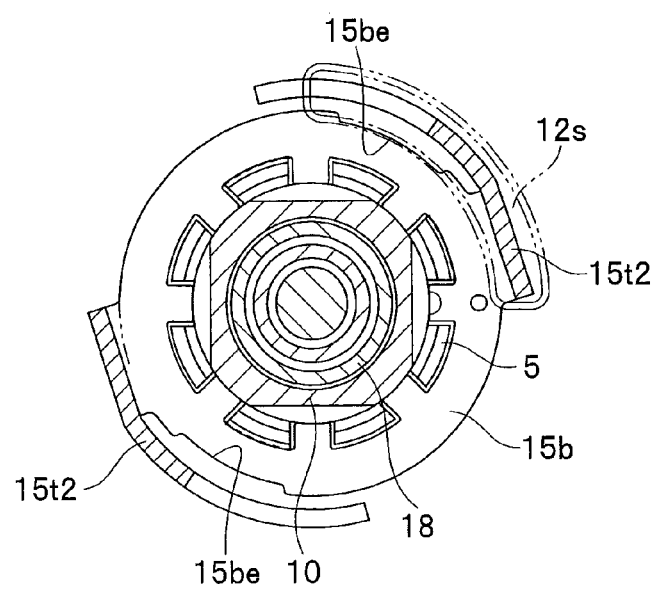
FIG. 12 is a partial sectional view of the bending operation apparatus taken along the XII-XII line in FIG. 2.
Figure 13:
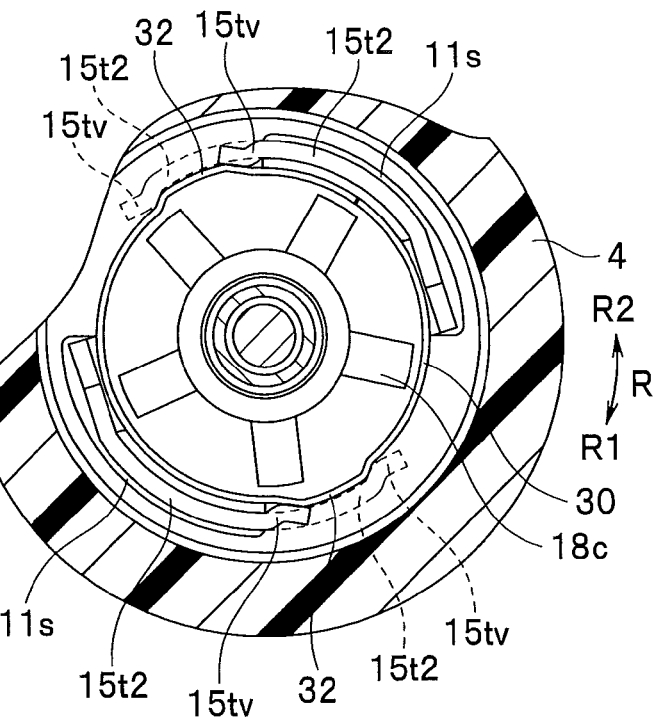
FIG. 13 is a partial sectional view of the bending operation apparatus taken along the XIII-XIII line in FIG. 2.
Figure 14:
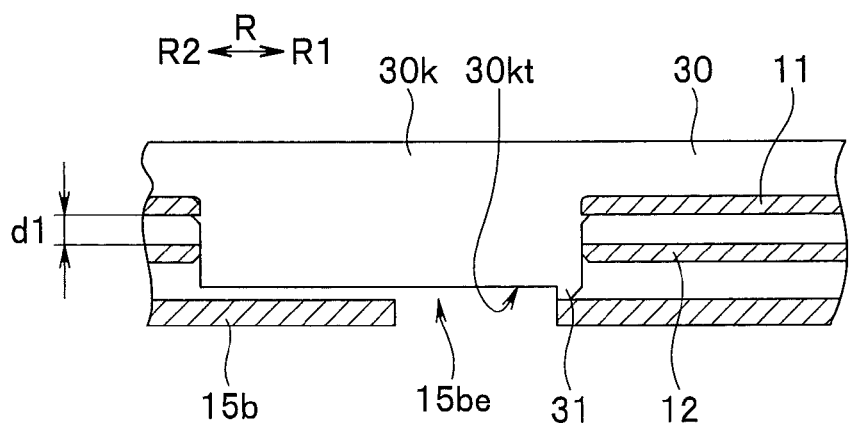
FIG. 14 is a partial sectional view showing a third position for the annular member in FIG. 2 along with a first position for the two movable disks.
Figure 15:
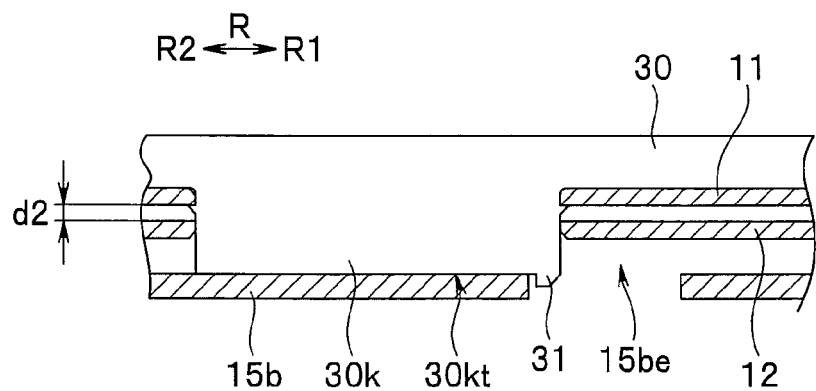
FIG. 15 is a partial sectional view showing a fourth position for the annular member in FIG. 2 along with a second position for the two movable disks.

FIG. 12 is a partial sectional view of the bending operation apparatus taken along the XII-XII line in FIG. 2. FIG. 13 is a partial sectional view of the bending operation apparatus taken along the XIII-XIII line in FIG. 2. FIG. 14 is a partial sectional view showing a third position for the annular member in FIG. 2 along with a first position for the two movable disks. FIG. 15 is a partial sectional view showing a fourth position for the annular member in FIG. 2 along with a second position for the two movable disks.

Note that the configuration of the bending operation apparatus 100 is described below by citing an exemplary configuration relating to the bending operation knob 4 and the fixing lever 5.

As shown in FIG. 2, the bending operation knob 4 is locked in an unfixed state to top portions 18c which serve as one end portion, separated from the operation portion 3 in an axial direction A, of a cylindrical pivoting shaft 18 provided by being extended along the axial direction A that is a direction substantially orthogonal to the inserting direction S from the inside of the operation portion 3. The bending operation knob 4 is rotatable in a direction R1 or R2 (see FIG. 3 for both) of the pivoting direction R along with the pivoting shaft 18. Note that the description of the structure of locking the bending operation knob 4 to the top portions 18c is omitted because such structure is well-known. The bending operation knob 4 may be fixed to the top portions 18c.

A lower end which is another end portion of the pivoting shaft 18 in the axial direction A, located inside the operation portion 3, is fitted to the sprocket 19 provided inside the operation portion 3. A chain (not shown) for bending the bending portion 2w is wound around the sprocket 19.

Thus, when the bending operation knob 4 is rotationally operated in the direction R1 or R2, the pivoting shaft 18 that is locked to the bending operation knob 4 in an unfixed state is also rotated in the same direction as that of the bending operation knob 4, and the sprocket 19 is also rotated in the same direction, so that pulling one of the sides of the chain causes the bending portion 2w to bend in an up or down direction.

Note that the configuration is not limited to the combination of the sprocket 19 and the chain, but may be a configuration in which the lower end of the pivoting shaft 18 is fitted to a pulley, and a wire wound around the pulley is pulled as the pulley is rotated.

Around an outer circumference in a radial direction K of the pivoting shaft 18, a cylindrical fixation shaft 10 extended along the axial direction A from the inside of the operation portion 3 is provided such that an upper end side which is an end portion separated from the operation portion 3 is inserted in a space 4i inside the bending operation knob 4. The fixation shaft 10 is formed along the axial direction A so as to have a polygonal sectional shape, a rectangular shape, for example, in the inserting direction S orthogonal to the axial direction A.

The fixation shaft 10 is fixed to a sheathing member 3g of the operation portion 3 via an O-shaped ring or the like, and is located coaxially with the pivoting shaft 18 having a predetermined space in the radial direction K with respect to the pivoting shaft 18, and thereby the fixation shaft 10 is irrotational with respect to the pivoting shaft 18.

Further, the fixing lever 5 is in contact with an outer circumference of the fixation shaft 10 so as to be pivotable in the pivoting direction R via O-shaped rings 21 or the like, the fixing lever 5 being located in the space 4i inside the bending operation knob 4 and formed of a resin material, for example.

Specifically, as shown in FIGS. 2 and 3, an inner circumferential surface of a ring-shaped portion 5b of the fixing lever 5 constituted of a grasping portion 5r and the ring-shaped portion 5b is in contact with an outer circumference of the fixation shaft 10 pivotably in the pivoting direction R via the O-shaped rings 21 or the like.

As shown in FIG. 2, an outer circumference of the ring-shaped portion 5b of the fixing lever 5 is in contact with an inner circumferential surface of the support plate 23 located in the space 4i inside the bending operation knob 4 via an O-shaped ring 22 or the like. An outer circumferential surface of the support plate 23 is in contact with an inner circumferential surface 4n of the bending operation knob 4 via an O-shaped ring 24 or the like.

Around the outer circumference of the fixation shaft 10, the cam member 15 which is located in the space 4i inside the bending operation knob 4 and is formed of a metal material, for example, is located coaxially with the fixing lever 5 in the axial direction A on an upper surface 4u side with respect to the ring-shaped portion 5b of the fixing lever 5.

As shown in FIG. 4, the main part of the cam member 15 includes a ring-shaped base portion 15b and two protruding portions 15t that are each protruded in an inverted-L-shape toward the upper surface 4u side in the axial direction A from the base portion 15b so as to face each other with respect to the axial direction A.

As shown in FIG. 3, the cam member 15 is fixed to the fixing lever 5 by a plurality of convex portions 15p protruded inward in the radial direction K from the base portion 15b being respectively fitted to a plurality of concave portions 5m formed on a surface on the cam member 15 side of the ring-shaped portion 5b of the fixing lever 5.

That is, the cam member 15 is pivotable in the direction R1 or R2 in the pivoting direction R along with the fixing lever 5 by fitting of the convex portions 15p to the concave portions 5m. In other words, the fixing lever 5 performs a pivoting operation for the cam member 15. Therefore, the cam member 15 is pivotable separately from the pivoting of the pivoting shaft 18.

As shown in FIG. 4, the main part of the protruding portions 15t of the cam member 15 includes raised portions 150 protruded toward the upper surface 4u side in the axial direction A, transverse portions 15t2 extended in a circular arc shape along the pivoting direction R in the direction R2 from protruding ends of the raised portions 15t1, and step portions 15t3 located on the direction R1 side of the raised portions 15t1.

As shown in FIGS. 4 to 6, cam grooves 15c are formed in the protruding portions 15t along the pivoting direction R between the base portion 15b and the transverse portions 15t2 in the axial direction A.

As shown in FIG. 5, the cam grooves 15c are formed to have inclined surfaces or circular-arc shaped surfaces such that a groove gap in the axial direction A decreases from m2 to m1 that is smaller than m2 (m2>m1) toward the direction R1.

Furthermore, as shown in FIGS. 4 and 13, extended ends on a direction R2 side of the transverse portions 15t2 of the protruding portions 15t are bent in a crank shape, whereby locking portions 15tv are formed.

As shown in FIGS. 4 and 12, cutouts 15be are formed in the base portion 15b of the cam member 15 so as to penetrate the base portion 15b in the axial direction A and have a predetermined length along the pivoting direction R respectively at positions which are symmetrical about a pivoting center of pivoting shaft 18, specifically, at positions facing the respective cam grooves 15c in the axial direction A.

Returning to FIG. 2, on the upper surface 4u side with respect to the base portion 15b of the cam member 15 in the outer circumference of the fixation shaft 10, an upper movable disk (hereinafter referred to as "movable disk") 11 on the top portions 18c side and a lower movable disk (hereinafter referred to as "movable disk") 12 that are formed of, for example, a metal material, specifically, a hard material such as stainless steel, are fixed in parallel so as to be located coaxially with the cam member 15 in the axial direction A, in the space 4i inside the bending operation knob 4. Note that the movable disks 11 and 12 are formed to have the same shape and the same size.

Specifically, as shown in FIGS. 3 and 10, in the movable disks 11, 12 are formed through-holes 11k, 12k that penetrate in the axial direction A, having an outer shape substantially equal to an outer shape of the fixation shaft 10, and a polygonal shape, for example, a rectangular shape, as seen in a plan view from the upper surface 4u side. The movable disks 11, 12 are fixed to the fixation shaft 10 inserted through the through-holes 11k, 12k.

The through-hole 11k of the movable disk 11 is formed in the same position as that of the through-hole 12k of the movable disk 12. That is, when the movable disk 11 and the movable disk 12 are superposed on each other, the through-holes 11k and 12k are superimposed each other. The positioning of the movable disks 11 and 12 in the pivoting direction R will be described later.

Thus the movable disks 11 and 12 are fixed to the fixation shaft 10, thereby being unpivotable with respect to the pivoting shaft 18 along with the fixation shaft 10.

Between the two movable disks 11, 12 in the axial direction A is provided a fixed disk 14 which is located coaxially with the two movable disks 11, 12 in the axial direction A and is located in the space 4i inside the bending operation knob 4.

The fixed disk 14 is in contact with the inner circumferential surface 4n of the bending operation knob 4 such that O-shaped rings 25 provided on an outer circumferential surface of the fixed disk 14 are set to have a shape and a pressing amount so as to generate a proper bending holding force with respect to the bending operation knob 4. The fixed disk 14 also has a flange portion 14f that is sandwiched by the two movable disks 11, 12 in the axial direction A in the second position (see FIG. 6) to be described later.

The O-shaped rings 25 may be discontinuously in contact with the inner circumferential surface 4n. The fixed disk 14 pivots along with the bending operation knob 4 in the first position (see FIG. 5) to be described later.

As shown in FIG. 4, in predetermined superimposed positions of the movable disks 11,12 as seen in a plan view from the upper surface 4u side, for example, in the axial direction A, two slits 11s and two slits 12s having a partial circular arc shape in the pivoting direction R are respectively formed in the respective disks 11, 12 so as to penetrate in the axial direction A, to be symmetrical about a pivoting center of the pivoting shaft 18, and to partially surround the respective through-holes 11k, 12k.

The slits 11s of the movable disk 11 are formed in the same positions as those of the slits 12s of the movable disk 12. That is, when the movable disks 11 and 12 are superposed on each other, the respective slits 11s and 12s are superimposed each other. The slits 11s, 12s are formed to be precisely positioned on the basis of the positions of the through-holes 11k, 12k.

The protruding portions 15t of the cam member 15 penetrate through the slits 11s, 12s to be movable in the direction R1 or R2 in the pivoting direction R separately from the pivoting shaft 18. That is, in a state where the protruding portions 15t of the cam member 15 have penetrated through the slits 11s, 12s, parts of the two movable disks 11, 12 are fitted in the cam grooves 15c.

The protruding portions 15t are movable in the pivoting direction R in the slits 11s, 12s between the position where the step portions 15t3 come into contact with opening end portions 12sk and the position where end portions 11sw, 12sw (see FIGS. 5 and 6) of the two movable disks 11, 12 come into contact with end portions 15ct of the cam grooves 15c.

Further, when the step portions 15t3 are in contact with the opening end portions 12sk, the two movable disks 11, 12 are separated from each other by the first gap d1 in the axial direction A as shown in FIG. 5. Hereinafter, the position in which the movable disks 11, 12 are separated from each other by the first gap d1 in the axial direction A will be indicated as the first position.

In the first position, the distal end side of the transverse portions 15t2 in the direction R2 is in contact with a top surface of the movable disk 11, and therefore, the protruding portions 15t do not come off the respective slits 11s, 12s toward the operation portion 3 side.

When the step portions 15t3 of the protruding portions 15t of the cam member 15 are in contact with the opening end portions 12sk in the first position shown in FIG. 5, the protruding portions 15t of the cam member 15 are restrained from rotating in the direction R1 with respect to the slit 12s.

As described above, the cam grooves 15c are formed in the protruding portions 15t in the pivoting direction R.

When the cam member 15 is rotated from the first position in the direction R2 which is one direction, the protruding portions 15t move in the direction R2 in the slits 11s, 12s until the end portions 11sw, 12sw of the slits 11s, 12s of the movable disks 11, 12 come into contact with the end portions 15ct of the cam grooves 15c in the pivoting direction R. With this movement, the movable disk 11 is guided by the inclined surfaces or the circular-arc shaped surfaces formed on the cam grooves 15c, and the rotational force is converted into the force in the axial direction A, whereby the movable disk 11 moves to the second position where the movable disk 11 is separated from the movable disk 12 by the second gap d2 that is shorter than the first gap d1 (d2<d1) in the axial direction A as shown in FIG. 6.

Namely, the cam grooves 15c have a shape that causes the movable disk 11 to move from the first position to the second position as the cam member 15 is rotated in the direction R2. The cam grooves 15c have a function of converting the rotational force into the force in the axial direction A and moving the movable disk 11 from the first position to the second position as the cam member 15 is rotated in the direction R2.

In the second position shown in FIG. 6, the flange portion 14f of the fixed disk 14 is sandwiched by the movable disks 11 and 12 in the axial direction A, whereby pivoting of the fixed disk 14 that pivots along with the bending operation knob 4 is fixed, and the O-shaped rings 25 come into contact with the inner circumferential surface 4n of the bending operation knob 4 with a frictional force.

By the frictional force, the pivoting position of the bending operation knob 4 is fixed. Note that at this time, the force with which the movable disks 11, 12 sandwich the flange portion 14f is greater than the frictional force between the bending operation knob 4 and the O-shaped rings 25.

As shown in FIGS. 2, 3 and 11, the respective slits 11s, 12s are penetrated through along the axial direction A by penetrating portions 30k of the annular member 30 located inside the respective protruding portions 15t in the radial direction K and located coaxially with the respective movable disks 11, 12 in the axial direction A. Note that the annular member 30 is formed of a metal material such as elastic stainless steel, for example.

Specifically, as shown in FIGS. 7 and 8, the annular member 30 has a ring shape with a predetermined length along the axial direction A. In predetermined positions of the annular member 30, which are symmetrical about the pivoting center of the pivoting shaft 18, respective inverted-concave-shaped clearances 30h are formed in positions where the annular member 30 are cut out along the pivoting direction R by a predetermined range so as to have openings on the operation portion 3 side. Thus, in predetermined positions symmetrical about the pivoting center of the pivoting shaft 18 where the clearances 30h are not formed in the annular member 30, the penetrating portions 30k are respectively formed to have a predetermined length of circular-arc in the pivoting direction R, a predetermined length in the axial direction A, and a shape to fit in the slits 11s, 12s.

As mentioned above, the penetrating portions 30k penetrate the slits 11s, 12s in the axial direction A inside the respective protruding portions 15t in the radial direction K, and are formed to have the same length of circular-arc as the length of circular-arc of the respective slits 11s, 12s in the pivoting direction R.

That is, both end portions 30km of the respective penetrating portions 30k in the pivoting direction R are formed to have a length with which the penetrating portions 30k contact the respective end portions 11sk, 11sw, 12sk and 12sw of the respective slits 11s, 12 (see FIGS. 3 and 10 for all of these elements) after the penetrating portions 30k penetrate the respective slits 11s, 12s. With this formation, the penetrating portions 30k accurately penetrate the respective slits 11s, 12s.

Besides, since the slits 11s, 12s are formed in the movable disks 11, 12 at precise positions on the basis of the positions of the through-holes 11k, 12k, the movable disk 12 is fixed on the outer circumference of the fixation shaft 10 in a state where the movable disk 12 is precisely positioned with respect to the movable disk 11 in the pivoting direction R.

That is, when the movable disks 11 and 12 are superposed each other, the respective through-holes 11k, 12k are superimposed in the precise position and the respective slits 11s, 12s are also superimposed each other in the precise position.

As shown in FIGS. 7 to 9, projecting portions 33 to which the movable disk 11 is locked are formed at the both end portions 30km of the penetrating portions 30k.

As shown in FIG. 8, the main part of the projecting portions 33 includes inclined surface portions 33s protruded toward the clearances 30h side with respect to the end portions 30km, and placement portions 33p that are between top portions of the inclined surface portions 33s and the end portions 30km, and are perpendicular to the axial direction A.

When the slits 11s are penetrated by the penetrating portions 30k, the movable disk 11 is fixed to the annular member 30 by the respective end portions 11sk, 11sw of the slits 11s going through the inclined surface portions 33s from the operation portion 3 side, and a bottom face 11x of the movable disk 11 being fitted so as to be placed on the placement portions 33p as shown in FIG. 9.

Such a formation of the placement portions 33p being perpendicular to the axial direction A prevents the movable disk 11 from coming off the projecting portions 33 toward the operation portion 3 side after the movable disk 11 is fixed.

With the movable disk 11 being fixed to the annular member 30, the annular member 30 is movable between a third position shown in FIG. 14 corresponding to the first position and the fourth position shown in FIG. 15 corresponding to the second position in the axial direction A, integrally with the movable disk 11 movable between the first position shown in FIG. 5 and the second position shown in FIG. 6, as the cam member 15 is pivoted in the pivoting direction R as described above.

As shown in FIGS. 8 and 10, at the end portions 11sk, 11sw, 12sk and 12sw of the slits 11s, 12s in the movable disks 11, 12, escape portions 11n, 12n protruded inward in the radial direction K are formed to cause the both end portions 30km of the penetrating portions 30k and the projecting portions 33 to escape inward in the radial direction K when the penetrating portions 30k penetrate through slits 11s, 12s.

As described above, the escape portions 11n, 12n are designed to, when the movable disk 11 is to be locked to the projecting portions 33 of the annular member 30, allow the both end portions 30km and the projecting portions 33 of the penetrating portions 30k of the annular member 30 to slightly elastically deform and escape inward in the radial direction, to permit easy flexure of the penetrating portions 30k in the slits 11s, thereby facilitating passage of the inclined surface portions 33s through the slits 11s and locking of the movable disk 11 to the projecting portions 33. In addition, after the movable disk 11 is locked, the escape portions 11n, 12n absorb the inward flexure in the radial direction K of the penetrating portions 30k in the slits 11s, 12s.

As shown in FIGS. 3, 7, 8 and 11, ridge portions 32 protruded outward in the radial direction K are formed on the outer circumferential surface 30g of the annular member 30 except the region of the penetrating portions 30k in positions symmetrical about the pivoting center of the pivoting shaft 18.

The ridge portions 32 are designed to apply a resistance force to the pivoting of the cam member 15, thereby preventing an unintended movement of the cam member 15 in the pivoting direction R in the first position or the second position.

Specifically, on one hand, as shown in FIG. 13, when the locking portions 15tv of the transverse portions 15t2 in the protruding portions 15t of the cam member 15 shown with a solid line are in contact with the inclined surfaces of the ridge portions 32 on the direction R1 side in the pivoting direction R, the two movable disks 11, 12 are in the state of having moved to the first position shown in FIG. 5, and thereby unintended rotation of the cam member 15 toward the direction R2 side is prevented by the locking portions 15*tv* being blocked by the inclined surfaces.

On the other hand, as shown in FIG. 13, when the locking portions 15*tv* of the transverse portions 15*t*2 in the protruding portions 15*t* of the cam member 15 shown with a broken line are in contact with the inclined surfaces of the ridge portions 32 on the direction R2 side in the pivoting direction R, the two movable disks 11, 12 are in the state of having moved to the second position shown in FIG. 6, and thereby unintended rotation of the cam member 15 toward the direction R1 side is prevented by the locking portions 15*tv* being locked by the inclined surfaces.

When the locking portions 15*tv* are moved in the pivoting direction R, the locking portions 15*tv* get over the ridge portions 32 to give a click feel to the operator, whereby the operator can easily recognize through the fixing lever 5 to which the cam member 15 is fixed that the movable disks 11, 12 have moved from the first position to the second position, or from the second position to the first position. That is, the ridge portions 32 notify the operator of completion of the movement of the movable disks 11, 12 with the click feel.

Further, as shown in FIGS. 7 to 9 and FIG. 13, step portions 31 protruded toward the operation portion 3 side are formed in positions on bottom portions 30*kt* of the penetrating portions 30*k*, the bottom portions 30*kt* being on an opposite side of the top portions 18*c*, the positions being close to the end portions 30*km* that are close to the inclined surfaces on the direction R1 side of the ridge portions 32.

In the fourth position for the annular member 30 shown in FIG. 15 which corresponds to the second position for the movable disks 11, 12 as shown in FIG. 6, the step portions 31 are not in contact with the base portion 15*b* by fitting in the cutouts 15*be* formed at the base portion 15*b* of the cam member 15 shown in FIGS. 4 and 12. The step portions 31 allow the position for the movable disks 11, 12 to be changed from the second position to the first position by coming into contact with the base portion 15*b* as shown in FIG. 14 in the third position for the annular member 30 which corresponds to the first position shown in FIG. 5, as the cam member 15 is rotated from the second position in the direction R1 which is the other rotation direction.

More specifically, in the fourth position for the annular member 30 shown in FIG. 15 corresponding to the second position for the movable disks 11, 12 shown in FIG. 6, the step portions 31 are fitted in the cutouts 15*be*, and the bottom portions 30*kt* of the penetrating portions 30*k* are in contact with the base portion 15*b* of the cam member 15. Further, in the third position for the annular member 30 shown in FIG. 14 corresponding to the first position for the movable disks 11, 12 shown in FIG. 5, rotation of the cam member 15 in the other direction R1 from the second position causes the step portions 31 to get on the base portion 15*b* from the cutouts 15*be*, with only the step portions 31 being in contact with the base portion 15*b* as shown in FIG. 14, thus causing the movable disk 11 to move toward the upper surface 4*u* side so as to separate from the fixed disk 14. Thus, the position for the movable disks 11, 12 is changed from the second position to the first position. That is, the step portions 31 enable the position for the movable disks 11, 12 to change from the second position to the first position.

Note that the descriptions are omitted regarding the above-described configurations relating to the bending operation knob 6 and the fixing knob 7 in the bending operation apparatus 100, since the bending operation apparatus 100 has the same configurations except that the fixing lever 5 is replaced with the fixing knob 7 and the bending operation knob 4 is replaced with the bending operation knob 6.

Next, actions of the present embodiment will be briefly described.

First, when bending the bending portion 2*w* of the insertion portion 2 in the up or down direction, the operator rotates the bending operation knob 4 locked to the top portions 18*c* of the pivoting shaft 18 in the direction R1 or R2 of the pivoting direction R as described above.

At this time, as shown in FIG. 14, since the step portions 31 formed at the bottom portions 30*kt* of the penetrating portions 30*k* of the annular member 30 are in contact with the base portion 15*b* of the cam member 15, the two movable disks 11, 12 in the bending operation knob 4 are in the first position shown in FIG. 5 where the movable disks 11, 12 do not sandwich the flange portion 14*f* of the fixed disk 14, and the O-shaped rings 25 provided on the outer circumference surface of the fixed disk 14 are in contact only with the inner circumferential surface 4*n* of the bending operation knob 4. The fixed disk 14 therefore pivots along with the bending operation knob 4, and thus the bending operation knob 4 can be easily rotated in the direction R1 or R2.

As a result, the pivoting shaft 18 fixed to the bending operation knob 4 and the sprocket 19 also rotates in the direction R1 or R2, which causes one of the sides of the chain wound around the sprocket 19 to be pulled, whereby the bending portion 2*w* is bent in the up or down direction. Note that at this time, the fixation shaft 10 does not pivot since the fixation shaft 10 is unpivotable with respect to the pivoting shaft 18.

The cam member 15 is prevented from being unintentionally rotated toward the direction R2 side since the locking portions 15*tv* of the transverse portions 15*t*2 of the protruding portions 15*t* of the cam member 15 are blocked by the inclined surfaces on the direction R1 side of the ridge portions 32 on the outer circumferential surface 30*g* of the annular member 30. That is, the first position of the movable disk 11, 12 is fixed.

Next, when the operator desires to fix the bending angle of the bending portion 2*w* in the up or down direction by the pivoting operation of the bending operation knob 4, that is, desires to fix the pivoting position of the bending operation knob 4, the operator rotates the fixing lever 5 in the direction R2 with respect to the fixation shaft 10.

As a result, the cam member 15 also rotates in the direction R2. Note that at this time, the fixation shaft 10, the two movable disks 11, 12 fixed to the fixation shaft 10, and the annular member 30 do not rotate in the direction R2.

Furthermore, in the slits 11*s*, 12*s* of the two movable disks 11, 12, the protruding portions 15*t* of the cam member 15 move in the slits 11*s*, 12*s* in the direction R2 until the end portions 11*sw*, 12*sw* of the slits 11*s*, 12*s* of the movable disks 11, 12 come into contact with the end portions 15*ct* of the cam grooves 15*c*.

Thus, the movable disk 11 is guided toward the movable disk 12 through the inclined surfaces or the circular-arc shaped surfaces formed on the cam grooves 15*c*, the rotational force is converted into the force in the axial direction A, and the movable disk 11 is moved from the first position shown in FIG. 5 to the second position where the movable disk 11 is separated from the movable disk 12 by the second gap d2 shorter than the first gap d1 in the axial direction A as shown in FIG. 6.

As the movable disk 11 is moved, that is, the cam member 15 is rotated in the direction R2, the step portions 31 formed at the bottom portions 30kt of the penetrating portions 30k of the annular member 30 to which the movable disk 11 is fixed are fitted in the cutouts 15be of the base portion 15b of the cam member 15, as shown in FIG. 15. In other words, the annular member 30 also moves from the third position shown in FIG. 14 to the fourth position shown in FIG. 15.

In accordance with the movement from the first position to the second position, the cam member 15 rotates in the direction R2 to cause the locking portions 15tv of the transverse portions 15t2 of the protruding portions 15t of the cam member 15 to get over the ridge portions 32 on the outer circumferential surface 30g of the annular member 30. This gives the operator the click feel through the fixing lever 5 and notifies the operator of the completion of the rotation of the cam member 15 in the direction R2.

After the movement, the locking portions 15tv are locked by the inclined surfaces on the direction R2 side of the ridge portions 32, thereby preventing the cam member 15 from being unintentionally rotated in the direction R1. That is, the second position of the movable disks 11, 12 is fixed.

Next, when the operator desires to release the fixation of the pivoting position of the bending operation knob 4, the operator rotates the fixing lever 5 in the direction R1 with respect to the fixation shaft 10. Thus also the cam member 15 rotates in the direction R1.

As a result, the step portions 31 of the bottom portions 30kt of the penetrating portions 30k of the annular member 30 get on the base portion 15b from cutouts 15be as shown in FIG. 14.

Consequently, the movable disk 11 fixed to the annular member 30 is surely moved from the second position shown in FIG. 6 to the first position shown in FIG. 5.

In this state, since the flange portion 14f is not sandwiched by the movable disks 11 and 12, the bending operation knob 4 is pivotable along with the fixed disk 14, and the fixation of the pivoting position of the bending operation knob 4 is released.

Note that at this time, there is a possibility that the movable disk 12 remains in contact with a bottom face of the fixed disk 14. However, the part of the fixed disk 14 that contacts the movable disk 11 is constituted of a member made of rubber or the like whose frictional force becomes greater due to the contact with the movable disk. Therefore, when the movable disk 11 is not completely separated from the fixed disk 14, there is a possibility that the frictional force is applied by the movable disk 11, and consequently, the frictional force is applied to the inner circumferential surface 4n through the fixed disk 14 even in the first position. However, since the part of the fixed disk 14 that comes into contact with the movable disk 12 is formed of a resin material or the like, even if the part is in contact with the movable disk 12, the frictional force would not be applied through the fixed disk 14 to the inner circumferential surface 4n since the frictional force from the movable disk 12 to the fixed disk 14 is small.

The bending operation knob 6 and the fixing knob 7 also have the same actions as those mentioned above.

In the foregoing, the present embodiment has described as follows. The slits 11s, 12s of the movable disks 11, 12 are penetrated in the axial direction by the penetrating portions 30k of the annular member 30 on an inner side in the radial direction K with respect to the protruding portions 15t of the cam member 15. The movable disk 11 is fixed to the annular member 30, and thereby the annular member 30 is movable along with the movable disk 11 in the axial direction A.

It is also described that the step portions 31 are formed at the bottom portions 30kt of the penetrating portions 30k of the annular member 30 so as to fit in the cutouts 15be of the base portion 15b of the cam member 15 in the fourth position for the annular member 30 corresponding to the second position of the movable disks 11, 12, and get on and come into contact with the base portion 15b of the cam member 15 in the third position for the annular member 30 corresponding to the first position for the movable disks 11, 12.

That is, the movable disk 11 moves from the second position to the first position by the step portions 31 getting on the base portion 15b from the cutouts 15be.

This allows the movable disk 11 fixed to the annular member 30 to surely and mechanically move to the first position separated from the fixed disk 14, by the step portions 31 only getting on the base portion 15b from the cutouts 15be as the cam member 15 is rotated in the direction R1.

Note that the bending operation knob 6 and the fixing knob 7 also provide the similar effects as those mentioned above.

It is thus made possible to provide the bending operation apparatus 100 for the endoscope having the configuration that can easily and surely prevent a resistance force from being applied to the pivoting of the bending operation knob 4 after the fixation of the pivoting position of the bending operation knob 4 is released, and provide the endoscope 1 including the bending operation apparatus.

The present embodiment may also have a configuration in which a spring is additionally provided in the space in the axial direction A between the movable disk 11 and 12, as in conventional arts, to more surely separate the movable disk 11 from the fixed disk 14 by the force of the spring in addition to the step portions 31 getting on the base portion 15b.

Further, the provision of the spring enables to more surely separate not only the movable disk 11 but also the movable disk 12 from the fixed disk 14, and to more surely fix the position of the movable disk 12 in the axial direction A in the first position.

The present embodiment, which has described that the movable disk 11 is fixed to the annular member 30, is not limited to this configuration, but the movable disk 11 may be formed integrally with the annular member 30.

Figure 16:
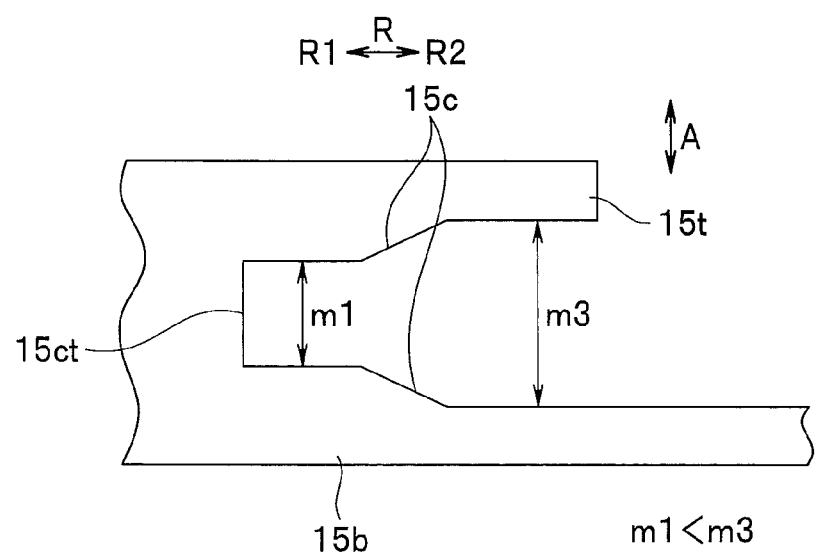
FIG. 16 is a view showing a modification example of the shape of the cam grooves formed at protruding portions of the cam member in FIG. 4.

Hereinafter, a modification example of the present invention will be described with reference to FIG. 16. FIG. 16 is a view showing the modification example of the shape of the cam grooves formed in the protruding portions in the cam member in FIG. 4.

It is described in the aforementioned present embodiment that the cam grooves 15c are formed between the transverse portions 15t2 and the base portion 15b, having the inclined surfaces or the circular-arc shaped surfaces, such that the groove gaps in the axial direction A decrease from m2 to m1 that is smaller than m2 (m2>m1) toward the direction R1 in the protruding portions 15t as shown in FIG. 5.

It is also described that the cam grooves 15c have a shape that allows the movable disk 11 to move from the first position to the second position as the cam member 15 is rotated in the direction R2. It is further described that the cam grooves 15c have a function of converting the rotational force into the force in the axial direction A and causing the movable disk 11 to move from the first position to the second position as the cam member 15 is rotated in the direction R2.

The present invention is not limited to this embodiment, but the cam grooves 15c may be formed into a shape that causes not only the movable disk 11 but also both the movable disks 11, 12 to move from the first position to the second position.

Specifically, as shown in FIG. 16, the cam grooves 15c may have a shape that causes both the movable disks 11, 12 to move from the first position to the second position as the cam member 15 is rotated in the direction R2 by being formed to have the inclined surfaces or the circular-arc shaped surfaces with respect to both the transverse portions 15t2 and the base portion 15b such that the groove gaps in the axial direction A decreases from m3 that is larger than m2 to m1 that is smaller than m3 (m3>m1) toward the direction R1.

In this case, the cam grooves 15c have the function of converting the rotational force into the force in the axial direction A and causing both the movable disks 11, 12 to move from the first position to the second position as the cam member 15 is rotated in the direction R2.

Such a configuration also allows the movable disk 12 to be surely separated from the fixed disk 14 in the first position.

What is claimed is:

1. A bending operation apparatus for an endoscope, the apparatus comprising:
    a bending operation knob that is pivotable with a pivoting shaft and performs a bending operation of a bending portion of the endoscope;
    a first movable disk that is provided inside the bending operation knob;
    a second movable disk that is movable between a first position in which the second movable disk is separated from the first movable disk by a first gap in an axial direction and a second position in which the second movable disk is separated from the first movable disk by a second gap that is shorter than the first gap in the axial direction;
    a cam member that is disposed in a position where the cam member contacts the second movable disk, the cam member causing an inclined surface formed on a cam groove to come into contact with the second movable disk as the cam member is pivoted in one direction, to move the second movable disk from the first position to the second position;
    a fixed disk that is disposed to be in contact with an inner circumferential surface of the bending operation knob, the fixed disk being sandwiched by the first movable disk and the second movable disk in the second position to apply a frictional force to pivoting of the bending operation knob;
    an annular member that is provided integrally with the second movable disk and is movable along with the second movable disk in the axial direction; and
    a step portion that is provided at the annular member, the step portion coming into contact with a base portion of the cam member as the cam member is pivoted in another direction opposite to the one direction, to cause the second movable disk to move from the second position to the first position.

2. The bending operation apparatus for the endoscope according to claim 1, wherein
    the first movable disk and the second movable disk each include a slit that penetrates in the axial direction, and
    the annular member further includes a penetrating portion that penetrates through the slit.

3. The bending operation apparatus for the endoscope according to claim 2, wherein the annular member further includes a projecting portion that is provided at an end portion of the penetrating portion in a pivoting direction to fix the second movable disk to the annular member.

4. The bending operation apparatus for the endoscope according to claim 3, wherein the first movable disk and the second movable disk each further include an escape portion that is provided at an end portion of the slit in the pivoting direction and is protruded inward in a radial direction, the escape portion being configured to cause the end portion of the penetrating portion in the pivoting direction to escape inward in the radial direction.

5. The bending operation apparatus for the endoscope according to claim 1, wherein the annular member is provided coaxially with the first movable disk and the second movable disk, and is disposed on an inside in the radial direction with respect to the cam member.

6. The bending operation apparatus for the endoscope according to claim 1, wherein the step portion is not in contact with the base portion by fitting in a cutout formed at the base portion of the cam member when the second movable disk is disposed in the second position.

7. The bending operation apparatus for the endoscope according to claim 1, wherein the cam member causes the first movable disk to move from the first position to the second position.

8. An endoscope comprising the bending operation apparatus for the endoscope according to claim 1.

* * * * *

UNITED STATES PATENT AND TRADEMARK OFFICE
CERTIFICATE OF CORRECTION

| | | |
|---|---|---|
| PATENT NO. | : 9,241,612 B2 | Page 1 of 1 |
| APPLICATION NO. | : 14/257276 | |
| DATED | : January 26, 2016 | |
| INVENTOR(S) | : Yuki Hoshino | |

It is certified that error appears in the above-identified patent and that said Letters Patent is hereby corrected as shown below:

Title Page, please insert

--(30) Foreign Application Priority Data

October 24, 2012 (JP).......................................2012-234942--

Signed and Sealed this
Twenty-sixth Day of April, 2016

Michelle K. Lee
*Director of the United States Patent and Trademark Office*